United States Patent [19]
Gielen et al.

[11] Patent Number: 6,011,996
[45] Date of Patent: Jan. 4, 2000

[54] DUAL ELECTRODE LEAD AND METHOD FOR BRAIN TARGET LOCALIZATION IN FUNCTIONAL STEREOTACTIC BRAIN SURGERY

[75] Inventors: Frans L. H. Gielen, Eckelrade; Victor P. J. Duysens, Grevenbicht; Johan F. M. Gijsberg, Munstergeleen, all of Netherlands

[73] Assignee: Medtronic, Inc, Minneapolis, Minn.

[21] Appl. No.: 09/009,247

[22] Filed: Jan. 20, 1998

[51] Int. Cl.[7] .......................................... A61N 1/05
[52] U.S. Cl. ............................................ 607/116; 600/378
[58] Field of Search .................... 607/116–118; 600/373, 600/378, 411, 417, 427, 429; 606/130

[56] References Cited

U.S. PATENT DOCUMENTS

| | | |
|---|---|---|
| 4,245,645 | 1/1981 | Arseneault et al. . |
| 4,850,359 | 7/1989 | Putz . |
| 4,852,573 | 8/1989 | Kennedy . |
| 5,464,446 | 11/1995 | Dressen et al. . |
| 5,713,847 | 2/1998 | Howard, III et al. ................... 607/116 |

*Primary Examiner*—William E. Kamm
*Assistant Examiner*—George R. Evanisko
*Attorney, Agent, or Firm*—Mike Jara; Harold R. Patton; Curtis D. Kinghorn

[57] ABSTRACT

A lead for brain target localization in functional stereotactic brain surgery, the lead having at its distal end a micro-electrode for use in recording single cell discharge patterns so as to identify functional boundaries between brain structures; and a macro-electrode for delivering test stimulation for determining target location for optimal therapeutic benefit and minimum side effects. The macro-test stimulation electrode is carried at the end of the lead length, and has a conventional surface area in the range of 1–20 mm$^2$ for stimulating chronic stimulation conditions. The micro-electrode is positioned at the distal end of an axially aligned probe which extends distally from the macro-electrode, and has a surface area adapted to enable a single cell recording; e.g., between 0.01 and 1000 $\mu$m$^2$. In an alternate embodiment, the tip micro-electrode is retractable so that the lead can be used for chronic brain stimulation.

14 Claims, 3 Drawing Sheets

DUAL ELECTRODE LEAD AND METHOD FOR BRAIN TARGET LOCALIZATION IN FUNCTIONAL STEREOTACTIC BRAIN SURGERY

FIELD OF THE INVENTION

This invention relates to a lead and method for brain target localization and, more particularly, a lead for combining a micro-electrode for single cell recording and a macro-test stimulation electrode for evaluation of an optimal site for placement of the chronic cranial stimulation electrode.

BACKGROUND OF THE INVENTION

Systems for providing electrical stimulation to an identified location in the brain for specific therapies are coming into increased use for various purposes. Specifically, such systems have been used for treating Parkinson's Disease Tremor and Essential Tremor. A typical electrical brain stimulation system comprises a pulse generator operatively connected to the brain by a lead. The lead has one or more stimulating electrodes at its distal end, designed to be implanted within the patient's brain at a precise location, so that the electrode or electrodes are optimally and safely positioned for the desired stimulation. Reference is made to U.S. Pat. No. 5,464,446, "Brain Lead Anchoring System," assigned to Medtronic, Inc., which is incorporated herein by reference, and which illustrates an effective lead anchoring system and discloses a method of positioning the stimulating lead so that the electrodes are at the desired stimulation site. The lead is positioned using a stereotactic instrument, which permits a very precise movement, e.g., ±1 mm, within the brain.

This invention addresses the initial step in functional stereotactic surgery, which is the localization or mapping of functional brain structures. It is to be noted that in many cases of Parkinson's Disease and Essential Tremor, the target is relatively easy to find, so that precise localization may not be necessary. However, other brain targets, such as in cases of advanced Parkinson's Disease, require the localization step. Generally, whenever the target is relatively new, in the sense of lacking statistical data which reliably identifies the target location, it is necessary to first determine where, within the boundary of the functional target area, stimulation can be delivered which is effective and which does not cause problems.

Therapeutic benefit and non-desired effects of brain lesioning and chronic neuromodulation depend critically on this localization procedures. This procedure involves three primary steps. First, anatomical localization of brain targets is determined using anatomical brain atlases, imaging by means of positive contrast x-rays, CT or MRI under stereotactic conditions. Thus, standard imaging techniques are used to make a first determination of coordinates for the lead's target. Next, electrophysiological identification of functional boundaries between brain structures is carried out by means of single cell recording of characteristic cell discharge patterns. This procedure requires use of an electrode which is small enough to differentiate single cells, and thus requires a micro-electrode with a very small surface area, e.g., less than one square micro-meter. The third step involves electrical test stimulation within determined functional brain structures, for the final evaluation of the efficacy of the location. Test stimulations are necessary to determine (1) efficacy of stimulation in the identified functional brain structure; and (2) any side effects caused by stimulation of the brain in this area. If the stimulation electrode is too close to the boundary of the functional brain structure, the function of adjacent brain structures will be modulated, which may lead to undesired side effects. The test stimulations are clinically most relevant when done with an electrode or electrodes with a similar surface area to that of the chronic implantable electrodes, e.g., in the range of about 1–20 square milli-meters.

As currently performed, the second and third steps, namely identification of functional boundaries with a micro-electrode and test stimulation with a larger, or macro-stimulation electrode, require first placement of the micro-electrode, withdrawal of same and then placement of the macro-electrode. These replacements require extra penetrations of the brain tissue, and therefore increase the risk of intra-cranial hemorrhages with severe permanent disability as a potential consequence. It has not been possible to perform effective test stimulation with the micro single cell electrode, because the volume of brain tissue that can be stimulated with the micro electrode is in general insufficient to evaluate efficacy and side effects. For example, our evaluation of functional stereotactic implantation of the Sub-Thalamic Nucleus (STN) or the Globus Pallitus Internae (GPi) reveals a discrepancy between electrical test stimulation with the micro single cell recording electrode and electrical stimulation with a chronic stimulation electrode. This discrepancy is most likely due to the very large difference of the electrode surface area, i.e., less than 1 square micro-meter vs. 1–20 square milli-meters, and the directly associated current density which results in stimulation of largely different volumes of cells, and therefore results in different therapeutic effects and side effects.

SUMMARY OF THE INVENTION

It is an object of this invention to provide a lead for use in functional stereotactic surgery for localization of functional brain structures, which combines a micro-electrode for identification of functional boundaries between brain structures and a macro-electrode for carrying out electrical test stimulation within functional brain structures. The macro-test stimulation electrode is positioned at the distal end of the lead casing, and has a conventional electrode surface area for stimulating electrodes in the range of about 1–20 square milli-meters. The micro-electrode is positioned at the distal end of a very narrow probe which extends distally from the macro-electrode, the micro-electrode being positioned on the tip end of the probe and having an electrode surface less than about 1000 square micro-meters, and preferably less than 1 square micro-meter. In an alternate embodiment, the micro-electrode is attached to a stylet which can be withdrawn after the localization procedure, enabling chronic use of the lead for brain stimulation.

In the use of the combined electrode lead of this invention, the lead is inserted into positions for single cell recordings by the micro-electrode, which recordings are not disturbed by the tissue displacement caused by the macro-test stimulation electrode also carried on the lead, proximally to the micro-electrode. Following each recording by the micro-electrode, a test stimulation is performed with the macro-electrode; the lead is advanced through the functional area of interest until all required recordings and test stimulations are performed, such that no subsequent brain penetration is required to complete the localization procedure.

DESCRIPTION OF THE PREFERRED EMBODIMENTS

Figure 1:
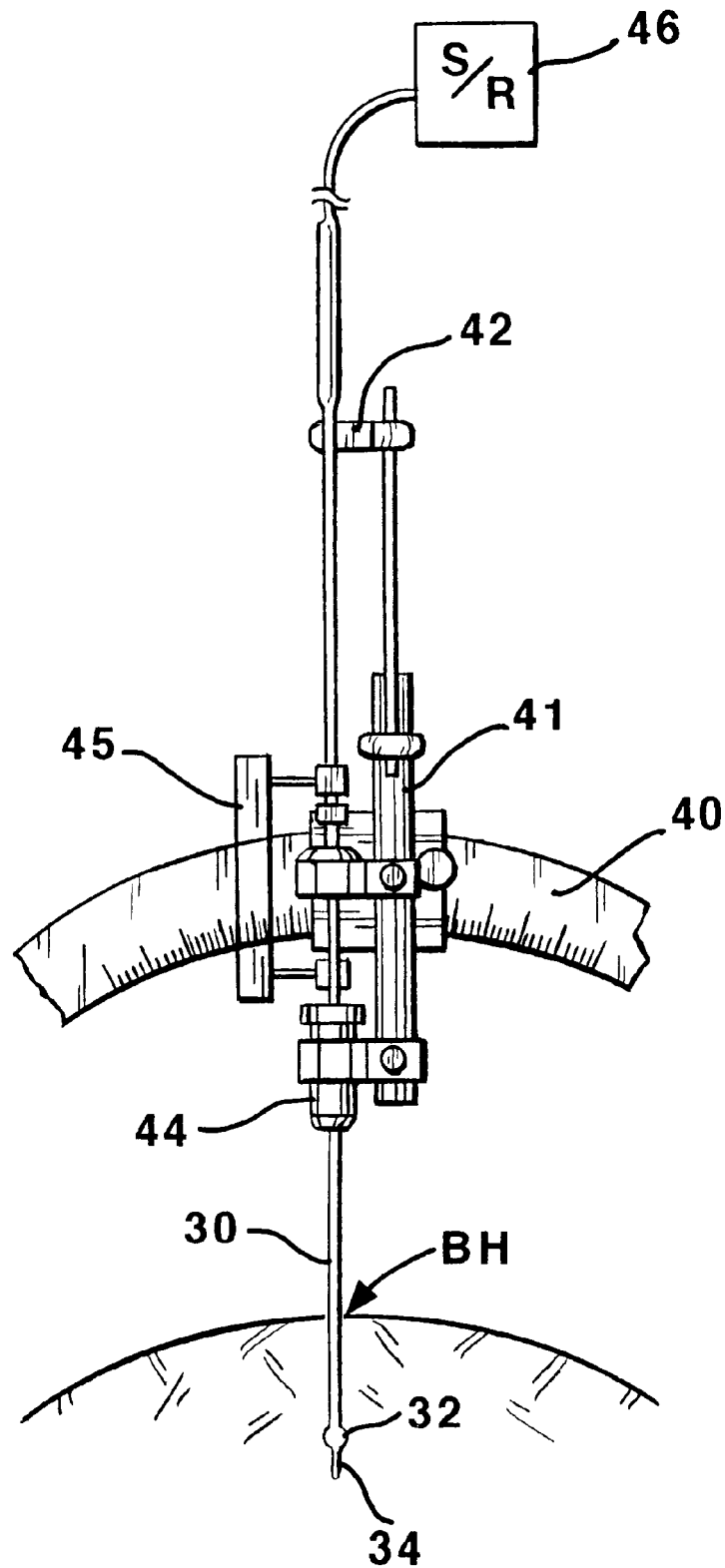
FIG. 1 is a system diagram showing a lead in accordance with this invention having its proximal end connected to a stimulator and recorder, the lead being in position so that single cell recordings and test stimulation can be carried out for locating the site for optimum chronic brain stimulation.

Referring now to FIG. 1, there is shown a schematic diagram of a brain lead 30, of the type of this invention, being held in position by a stereotactic instrument. The stereotactic instrument is a commercially available device, and has a frame shown partially at 40. The frame carries a lead holder assembly indicated at 41, which in turn supports a lead holder 42. The lead 30 is positioned through the lead holder and through the guide tube as shown at 44. A micro-positioner, shown schematically at 45, is used to advance the lead one cell at a time. The distal end of the lead is shown schematically to have a first larger, or macro-electrode 32 at the lead distal end, and distal to that a micro-electrode 34. As illustrated, the distal end of the lead is inserted through a burr hole in the skull of the patient, illustrated diagrammatically by BH. The proximal end of the lead is connected to an appropriate stimulator and recorder, as illustrated diagrammatically at 46. The technique for positioning a cranial lead with a stereotactic instrument is well known in the art.

Figure 2:
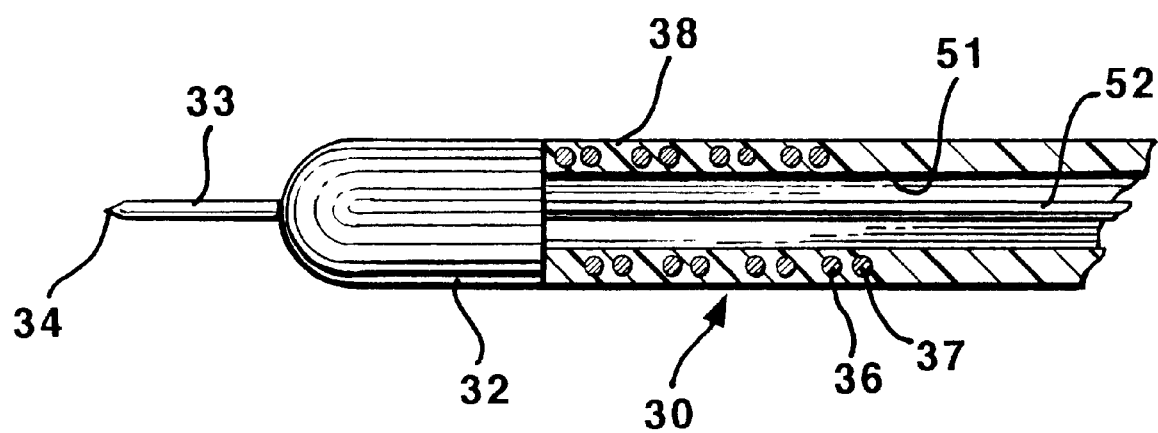
FIG. 2 is a schematic diagram of the distal end of the lead of this invention, illustrating the micro-electrode and macro-electrode.

Referring now to FIG. 2, there is shown an exploded detailed view of the far distal end of a lead 30 in accordance with this invention. As illustrated, a macro-electrode 32 is positioned at the distal end of the casing 38. Electrode 32 may have the shape and surface area of a conventional cranial stimulus electrode, the surface area preferably being in the range of 1–20 mm$^2$. Extending axially distal from electrode 32 is a thin probe 33, terminating in a micro-electrode 34, having a surface area less than 1000 $\mu$m$^2$, and preferably less than 1 $\mu$m$^2$. For example, electrode 34 may have a surface area of 500–100 $\mu$m$^2$ for a semi-micro-electrode, and a surface area less than 1 $\mu$m$^2$ for a micro-electrode e.g., 0.01 $\mu$m$^2$. The length of probe 33, i.e., from the distal-less surface of electrode 32 to the micro-electrode 34, is suitably in the range of 1 to 10 mm, and preferably about 2–5 mm. The length of this probe is important, as it establishes the distance between the two electrodes. This distance is important, since the larger electrode 32 should be sufficiently remote so that its penetration does not perturb the cells that are being probed by micro-electrode 34. Conductors 36, 37 are illustrated as coils which connect from the proximal end of the lead to electrodes 32, 34 respectively; electrode 34 is electrically connected through the interior of probe 33. Tube casing 38, made of conventional biocompatible material, encapsulates the length of the lead in a known manner. Insulating sleeve 51 retains the coils, establishing an axial lumen. As illustrated, a stylet 52, suitably made of tungsten, connects mechanically to probe 33, so that the micro-tip electrode 34 can be withdrawn.

The lead is, in the preferred embodiment, designed for use only as a test lead, and thus does not need to be designed for permanent implantation. Material choices are a function of whether the lead is to be resterilized, or disposable after one patient use. The macro-electrode 32 can be made of typical acute stimulation electrode material, e.g., stainless steel, Pt Ir, or Pt. The micro-electrode needs to be durable for at least one trajectory, as described below, but preferably 1–10 trajectories; the electrode material can be, e.g., tungsten, Pt Ir, or Ir. The lead must be stereotactically rigid, and of sufficient length to reach the target area of the brain. Since the radius of a typical stereotactic frame is 190 mm, and the lead needs the ability to go further to reach the target with a margin of safety, the lead should be greater than about 30 cm in length.

Figure 3:
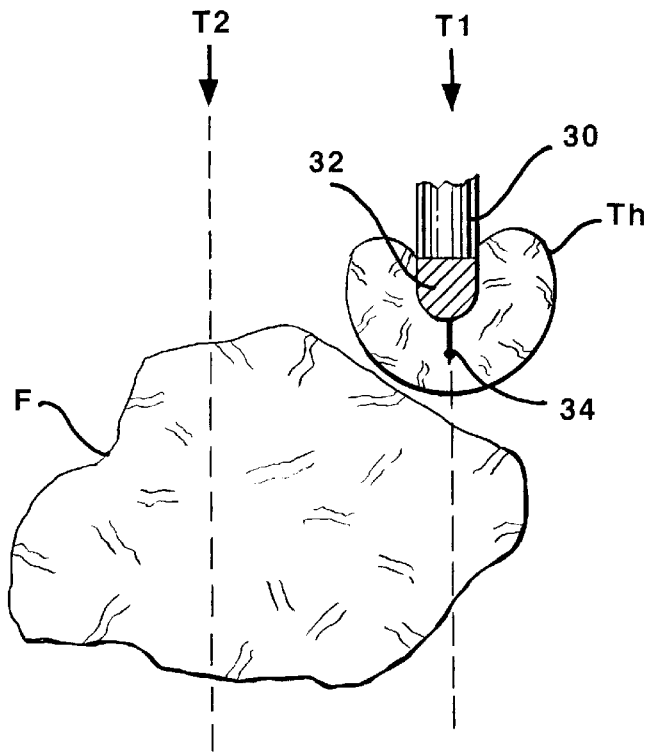
FIG. 3 is a schematic illustration of trajectories taken by the distal end of the lead for recording and test stimulating.

Referring now to FIG. 3, there is shown a diagrammatic representation of two test trajectories taken relative to a functional portion of the patient's brain, the functional portion being defined by a boundary F. Two illustrative trajectories are shown as indicated at T1 and T2. The distal end of the lead 30 is illustrated with respect to T1, with the micro-electrode 34 and macro-electrode 32 being illustrated. The line indicated as $T_H$ indicates the distance from the macro-electrode 32 at which current density delivered by a test stimulus pulse is above the threshold for stimulation. As the tip is moved along trajectory T1 indicated by dashed lines, through the functional structure, cell recordings are taken by micro electrode 34, and test stimulus pulses are delivered through macro-electrode 32. Knowing the threshold pattern and the distance between the two electrodes, the physician can verify which recorded cells corresponds to good efficacy without non-wanted side effects. As can be seen, for trajectory T1, no cell locations correspond to a position where adjacent brain structure would not be stimulated. However, for trajectory T2 there is ample room within the functional structure where delivered stimulus pulses will effect the target brain area without stimulating adjacent brain structures outside of the functional area.

Figure 4:
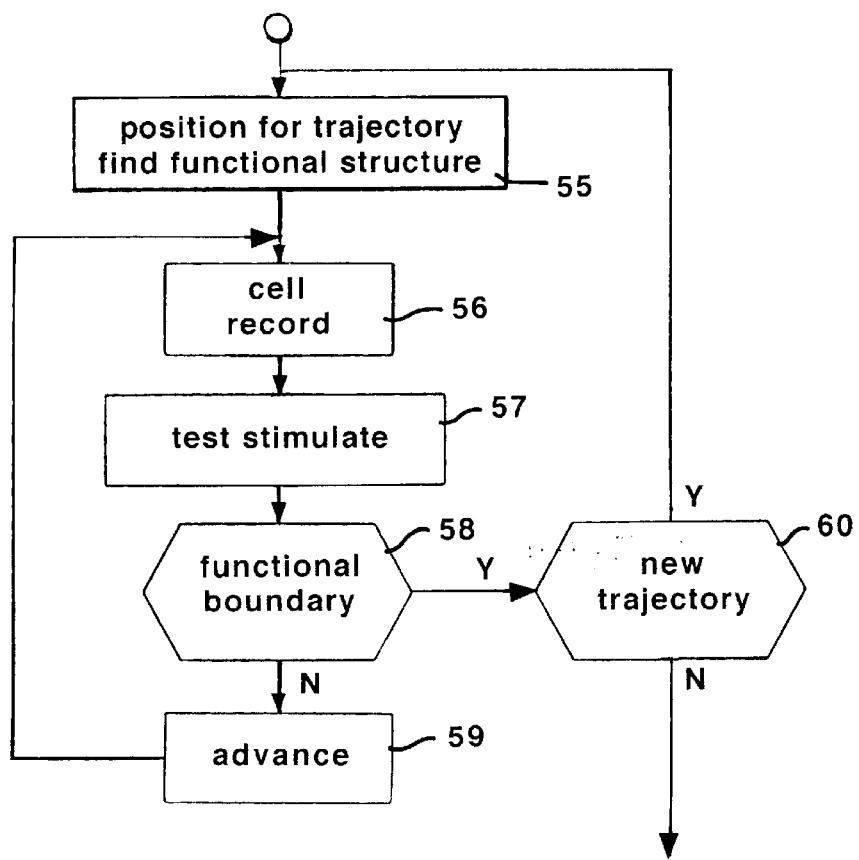
FIG. 4 is a flow diagram showing the primary steps taken in using the combined electrode lead of this invention for making single cell recordings and carrying out electrical test stimulation.

Referring to FIG. 4, there is shown a flow diagram outlining the primary steps taken in carrying out a localization procedure with the lead of this invention. At 55, the lead is positioned for a trajectory, e.g., trajectory T1 or T2 as indicated in FIG. 3. The lead is advanced until the micro-electrode 34 discovers the boundary F of the functional structure, i.e., there is a recording of a cell corresponding to the functional structure involved. At 56, a cell recording is made, and then at 57 a test simulation pulse is delivered, and it is determined whether a stimulation is efficacious and without side effects. Next, it is determined whether the cell recordation indicates that a functional boundary has been passed, e.g., micro-electrode 34 has passed out of the functional structure area. If no, the lead is advanced to the next cell, as indicated at 59, by the micro-positioner 45, and the cycle is repeated. When, at step 58, the trajectory has been determined to have completed the path through the functional area, it is determined at 60 whether a new trajectory is to be done. If yes, steps 55–59 are carried out in the same manner. As indicated above, in any particular case a number of trajectories may be required, in order to find a suitable stimulus location.

Following the localization procedure at FIG. 4, and determination of a suitable location for chronic stimulation, the lead can be withdrawn. In another embodiment, micro-electrode 34 may be attached to a movable stylet 52, which can be withdrawn while holding macro-electrode 32 at the target position. In such case, the lead is fixed with respect to the patient's skull in a manner as referenced above, whereafter chronic stimulation can be carried out, generating and delivering stimulus pulses through the lead and macro-electrode 32. Accordingly, the lead of this invention can be used solely as a test lead that can be disposed of after the localization procedure, or may be designed both for the test procedure and for chronic stimulation.

We claim:

1. A lead for brain target localization, comprising a proximal end and a distal end with a length therebetween, a casing covering the lead over said length, first and second conductors within said casing extending between said proximal and distal ends, and a first stimulating electrode at said distal end and connected to said first conductor, said first electrode having a surface area in the range of about 1–20 mm$^2$; and a probe element extending more than 1 mm distally from said first electrode and carrying a micro-electrode at the probe element distal tip, said micro-electrode having a surface area in the range of 0.01 to 1000 $\mu$m$^2$, and being connected to said second conductor.

2. The lead as described in claim 1, wherein said probe has a length in the range of about 1–10 mm.

3. The lead as described in claim 2, wherein said lead length is substantially cylindrical, and said probe is positioned along the center axis of said lead.

4. The lead as described in claim 3, wherein said probe is less than about 0.2 mm in thickness.

5. The lead as described in claim 1, wherein said first electrode has a cylindrical surface congruent with said lead casing.

6. The lead as described in claim 1, wherein said micro-electrode has a surface area of less than 1 $\mu$m$^2$.

7. The lead as described in claim 1, wherein said micro-electrode has a surface area in the range of 500 to 1000 $\mu$m$^2$.

8. The lead as described in claim 1, comprising a stylet attached to said probe element, whereby said probe element can be withdrawn from said lead.

9. The lead as described in claim 1, wherein said length is at least 300 mm.

10. A system for brain target localization, comprising a stereotactic instrument mountable on a patient's head, a lead comprising a proximal end and a distal end with a length therebetween for use in brain target localization, first and second conductors extending between said proximal and distal ends, a micro-positioner for positioning said lead when held by said stereotactic instrument so that said lead distal end is movable within the patient's brain, stimulation means for delivering test stimulation pulses through said lead, and recording from said lead means for recording cell discharge patterns, said lead further comprising:

a first stimulating electrode at said distal end and connected to said first conductor, said first electrode having a surface area in the range of about 1–20 mm$^2$; and a probe element extending more than 1 mm distally from said first electrode and carrying a micro-electrode at the probe element distal tip, said micro-electrode having a surface area in the range of 0.01 to 1000 $\mu$m$^2$, and being connected to said second conductor.

11. The system as described in claim 10, wherein said micro-electrode has a surface area of less than 1 $\mu$m$^2$.

12. The system as described in claim 10, wherein said micro-electrode has a surface area in the range of 500 to 1000 $\mu$m$^2$.

13. The system as described in claim 10, comprising a stylet attached to said probe element, whereby said probe element can be withdrawn from said lead.

14. The system as described in claim 10, wherein said length is at least 300 mm.

* * * * *